(12) United States Patent
Heinz et al.

(10) Patent No.: US 6,190,343 B1
(45) Date of Patent: Feb. 20, 2001

(54) CRUCIFORM ANTERIOR SPINAL HYPEREXTENSION ORTHOSIS

(75) Inventors: Thomas J. Heinz, Flintridge; Dae Shik Park, Fullerton, both of CA (US)

(73) Assignee: Bio Cybernetics International, Pasadena, CA (US)

( * ) Notice: Under 35 U.S.C. 154(b), the term of this patent shall be extended for 0 days.

(21) Appl. No.: 09/458,964

(22) Filed: Dec. 10, 1999

(51) Int. Cl.[7] ...................................................... A61F 5/24
(52) U.S. Cl. ............................................................ 602/19
(58) Field of Search ............................. 606/53, 54, 237; 602/19

(56) References Cited

U.S. PATENT DOCUMENTS

| | | | |
|---|---|---|---|
| Re. 31,564 | * | 4/1984 | Hendricks . |
| Re. 35,940 | * | 10/1998 | Heinz et al. ............................. 602/19 |
| 2,808,050 | * | 10/1957 | Ward ...................................... 602/19 |
| 5,135,471 | * | 8/1992 | Houswerth ............................. 602/19 |
| 5,599,287 | * | 2/1997 | Beczak, Sr. et al. .................. 602/19 |
| 6,010,472 | * | 1/2000 | Schiller ................................. 602/19 |

* cited by examiner

Primary Examiner—Jeffrey A. Smith
(74) Attorney, Agent, or Firm—Arent Fox Kintner Plotkin & Kahn, PLLC

(57) ABSTRACT

A cruciform anterior spinal hyperextension orthosis comprising a front portion having a rigid anterior cruciform brace assembly provided with movable upper and lower arms extending therefrom and arranged vertically, two laterally disposed movable arms extending therefrom horizontally, and body contact pads rotatably secured to the free ends of each of the upper and lower vertically disposed arms. A rear portion is provided adjustably secured to the front portion and having a paraspinal support formed in two juxtaposed segments, a pulley system comprising at least one pulley set having two pulley banks each having a plurality of pulleys, each bank disposed proximate to an adjacent edge of the juxtaposed segment, and a cable running through each pulley of each bank of pulleys in the set in alteration and in series and linking together each of the two juxtaposed segments. Adjustable mechanism for securing the front portion to the rear portion including: two straps, respectively removably attached to lateral edges of the two juxtaposed segments and adapted to be secured to two strap engaging devices, respectively, attached to each of the laterally disposed movable arms.

10 Claims, 3 Drawing Sheets

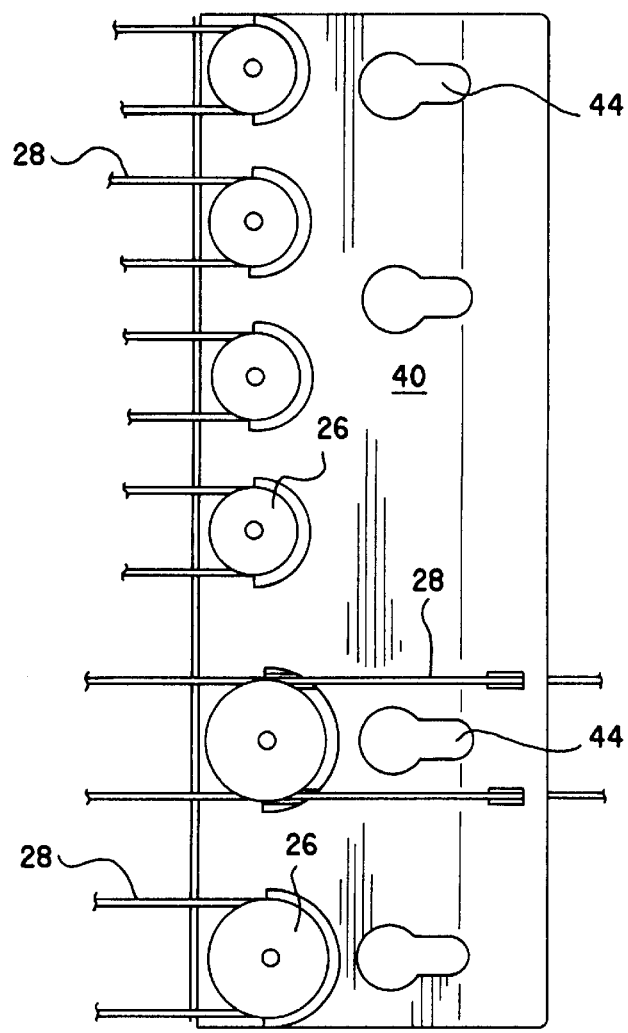
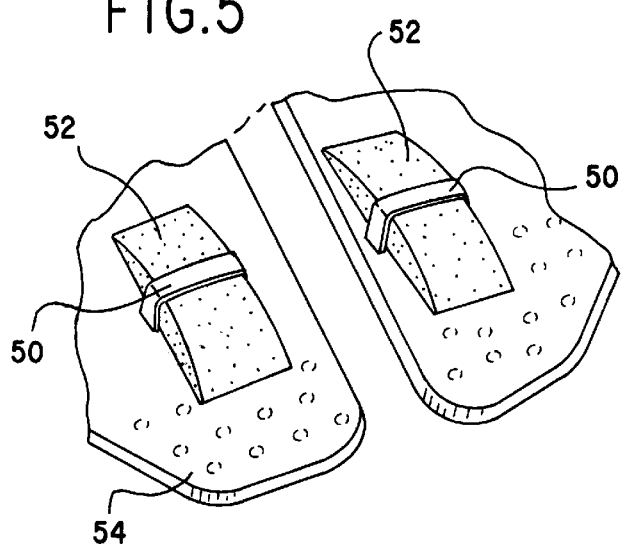

CRUCIFORM ANTERIOR SPINAL HYPEREXTENSION ORTHOSIS

TECHNICAL FIELD

The invention relates to orthotic devices used in the treatment of spinal disorders and/or used subsequent to surgery where forward flexing of the torso is to be minimized. More particularly, the invention relates to orthotic devices employed for partial or substantial immobilization of portions of the torso and having multiple modes of adjustment facilitating both rapid donning and doffing and individualized adjustment to custom fit the user of the device.

BACKGROUND ART

A common method of alleviating pain in people suffering from back injuries and promoting healing in post-operative back surgery patients is to stabilize the spine by means of an orthosis, such as a brace. Such braces include a multitude of materials and designs which can be snugly fitted around the patient's trunk. In certain applications, the back portion of the orthosis may be provided with pockets into which are inserted lordotic pads for treating spinal lordosis.

Such braces are effective in achieving spinal stability if worn properly and consistently; however, most patients have difficulty in manually adjusting the brace to fit tightly enough to provide adequate support. This is especially true in the case of post-operative and older patients who are generally in pain and frequently lack sufficient strength to make the necessary adjustments. For many patients suffering spinal ailments, these braces are also difficult to don and doff, appropriately position and fasten and subsequently remove. In addition, because of the structures of many of these devices and/or the choice of materials used in their construction, the orthoses are quite uncomfortable, in many instances inducing extensive perspiring and/or chafing. Without being consistently worn and properly adjusted, such patient non-compliance obviously reduces the effectiveness of the device.

Another frequently encountered problem with these types of orthoses is their inability to conform to the torso as the patient moves from a standing to a sitting position or vice versa. Thus, although such a device may have been initially properly adjusted, once the patient has changed position, it may be necessary to make additional adjustments manually to vary the tension, depending on whether the patient is standing or sifting. Similar situations and corresponding adjustments may be required as, or shortly after, a meal is consumed or digested.

Advances have been made in recent years to provide orthotic devices which can be more easily adjusted to the individual patient and readjusted when their physical position changes. Thus, in U.S. Pat. No. Re 35,940 an electromechanical back brace apparatus is described which is provided with an electromechanical mechanism for tightening the brace around the trunk of the patient to a desired tension. A cable and pulley arrangement is tightened by a small motor to provide the desired tension in the brace. A microprocessor is also provided to control the motor to obtain desired repeatable tension settings. While such a device facilitates rapid and repeatable adjustment of such a brace, the inclusion of an electromechanical mechanism and a microprocessor increases the cost of such a device to a patient or to their medical insurance program. In addition, there is the need to periodically replace batteries to power the electrically operated components.

In the treatment of certain specific abnormalities of the spine and some postoperative conditions, a cruciform anterior spinal hyperextension orthosis is well known and has been widely used with success. For example, in many instances, the condition of a patient requires that their torso be immobilized so that they do not bend the upper torso forward. With such devices used heretofore, a common type of cruciform anterior spinal hyperextension system applies pressure to the front or anterior of the thoracic and pubic areas of the human body in combination with a back pad and straps or similar arrangement in order to tension the front and back structures to cause hyperextension of the posterior lumbar region of the body. Typical devices include a front structure having upper and lower arms and right and left arms, the upper and lower arms including an appropriate pad to be placed in contact on the sternal and pubic areas of the human body. The front structure is combined with a back or lumbar pad, the latter being adjustably connected to the left and right arms by straps or similar arrangement. The device may be suitably tensioned to apply the necessary forces to hyperextend the patient's back. Frequently, the problems associated with such devices are that they are generally difficult and time consuming to adjust and readjust.

Accordingly, it is an object of the present invention to provide orthotic devices which result in greater patient compliance since the key to successful orthotic treatment is patient compliance. The attributes of an effective orthotic device which induces patient compliance includes ease of donning an doffing the device, ease of adjusting the device, comfort to the wearer of the device, and effective heat dissipation. More specifically, it is a primary object of this invention to provide orthoses which may be tightened around the torso of a patient to provide the necessary support and immobilization of the spine with the minimal physical effort required on the part of the patient.

It is a further object of the present invention to include individual controls for adjustment and custom fitting of different parts of the orthotic device.

It is another object of the present invention to provide multiple modes of adjustment to achieve individualized adjustment of various portions of orthosis. It is still another object of the present invention to provide multiple and independent means of adjustment of various portions of an orthotic device.

It is yet another object of the present invention to provide a rigid orthotic apparatus having a significant mechanical advantage that may be individually adjusted to a desired tension. It is yet another object of the present invention to provide a cruciform anterior spinal hyperextension which includes multiple means of adjustment for individually fitting the orthosis to a patient.

It is another object of the invention to provide an orthotic device which is capable of being rapidly adjusted and, where appropriate, readjusted to an appropriate tension. It is another object of the present invention to allow the orthotic device to be easily dissembled to clean component parts of the device. It is another object of the invention to provide orthoses which are easily donning and doffed. It is also an object of the invention to provide orthoses which are comfortable and which have minimal points of contact with a patient's body, thereby minimizing chafing.

It is a further object of the present invention to provide a cruciform anterior spinal hyperextension orthosis which contacts the human body at three points, the lumbar region of the back, the sternum and the pubic area.

It is still another object of the invention to provide a cruciform anterior spinal hyperextension system having a rear portion which serves as both as a paraspinal support which also incorporates a means for adjusting the orthosis.

DISCLOSURE OF INVENTION

The present invention is directed to braces and orthotic devices which result in significantly increased patient compliance. This is attributable to orthoses that are both easily donned and doffed as well as being easily and rapidly adjustable to accommodate changes in the position of a wearer of the device. The orthotic devices of the invention include multiple modes of adjustment which are independently adjustable to accommodate and conform to varying physical profiles of a user of the device as well as to accommodate a change in the position of the torso about which the devices are secured. The devices of the invention provide greater patient comfort and adjustability and result, therefore, in greater patient compliance. Preferably, component parts of the devices may be easily dissembled and assembled for cleaning.

The orthotic devices of the present invention, include an orthosis or brace body adapted to be wrapped around the torso or trunk of a user, the brace body including at least two segments.

The present invention includes a front portion having a rigid cruciform structure provided with a generally rigid anterior cruciform assembly having upper and lower moveable arms extending therefrom and arranged vertically and two laterally disposed movable arms extending therefrom disposed horizontally. Rotatably secured to the free ends of each of the upper and lower vertically arranged arms are body contact pads, the upper pad adapted to be placed in contact with the sternum of a patient and the lower pad adapted to be placed in contact with the pubic region of the patient. At the free ends of the horizontally disposed movable arms are located means for securing the front cruciform structure with a rear or posterior portion. The posterior portion includes a posterior contact portion and a means for adjusting the tightness or tension of the cruciform anterior spinal hyperextension orthosis.

Preferably, the rear portion includes two segments spaced from one another and a means for adjusting the device which permits the patient to adjust the distance between the two segments. Preferably, the means for adjusting the distance between the two segments includes at least one set of pulleys having separate banks of pulleys, each bank being mounted on opposing segments in facing relationship and each set of pulleys includes a plurality of individual pulleys. The two segments are linked together by a cable which is run through each pulley of each bank of pulleys in a set in alteration and in series.

The two segments may be physically separate pieces or can be regions of the same rear portion of the device.

In a preferred embodiment of the invention, the free ends of the cable joining the two banks of a pulley set are secured to a handle, which when pulled increases the tension of the cable and draws the two segments of the rear portion to which the separate banks of pulleys are mounted together.

BRIEF DESCRIPTION OF DRAWINGS

Other objects, features and advantages will become evident in light of the following detailed description, considered in conjunction with the referenced drawings of preferred embodiments according to the present invention. It should be understood that these drawings are exemplary only and should not be construed as limiting the invention in any way.

FIG. 4 shows a bank of a modular pulley set used in the invention with its cover removed; and FIG. 5 shows an enlarged portion of the embodiment of the present invention illustrated in FIG. 1 with a bank of a set of a preferred pulley system removed from its corresponding segment of the orthotic device, revealing the underside of the pulley bank.

MODES FOR CARRYING OUT THE INVENTION

Figure 1:
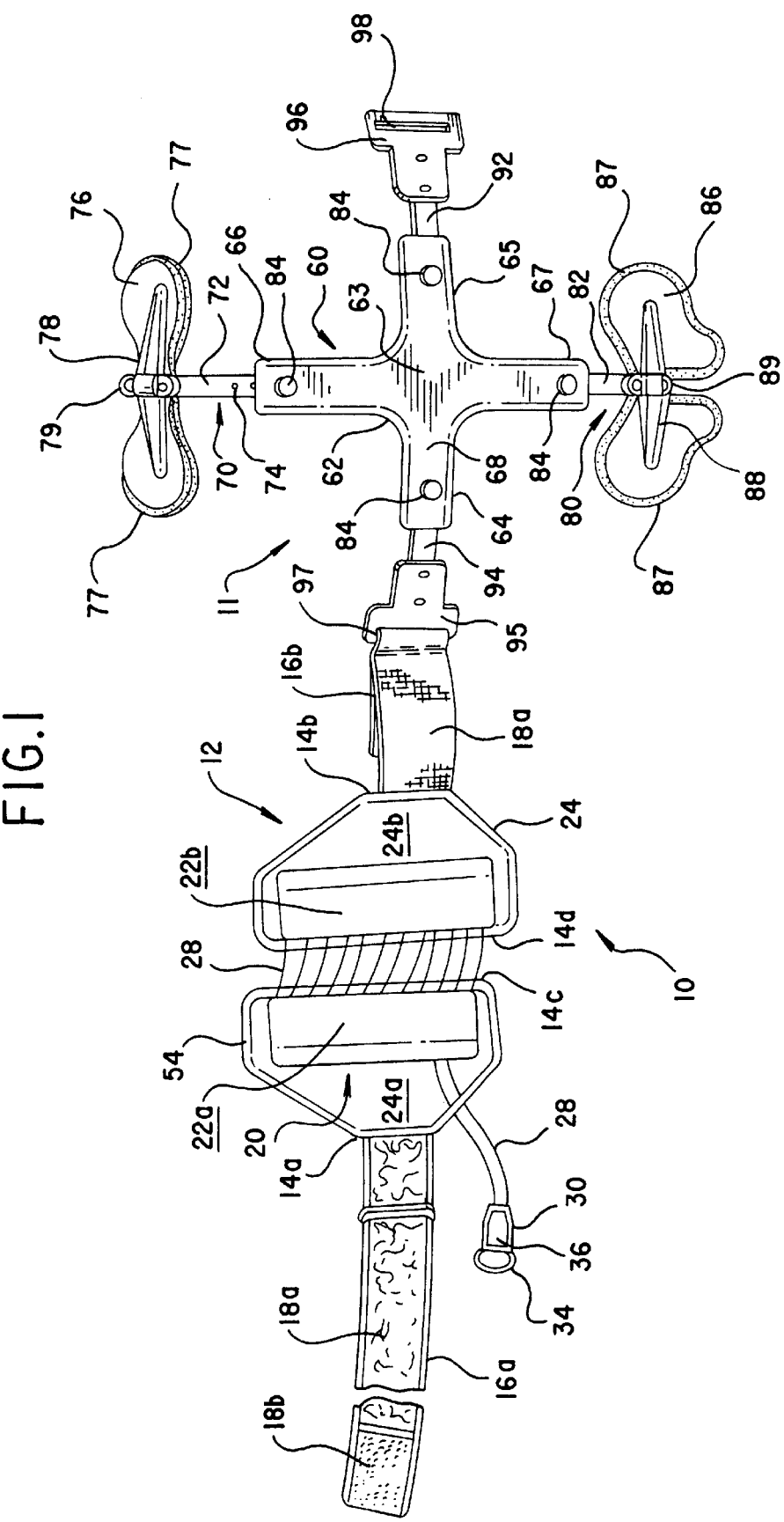
FIG. 1 shows a plan view of an outer side of an embodiment according to the present invention.
Figure 2:
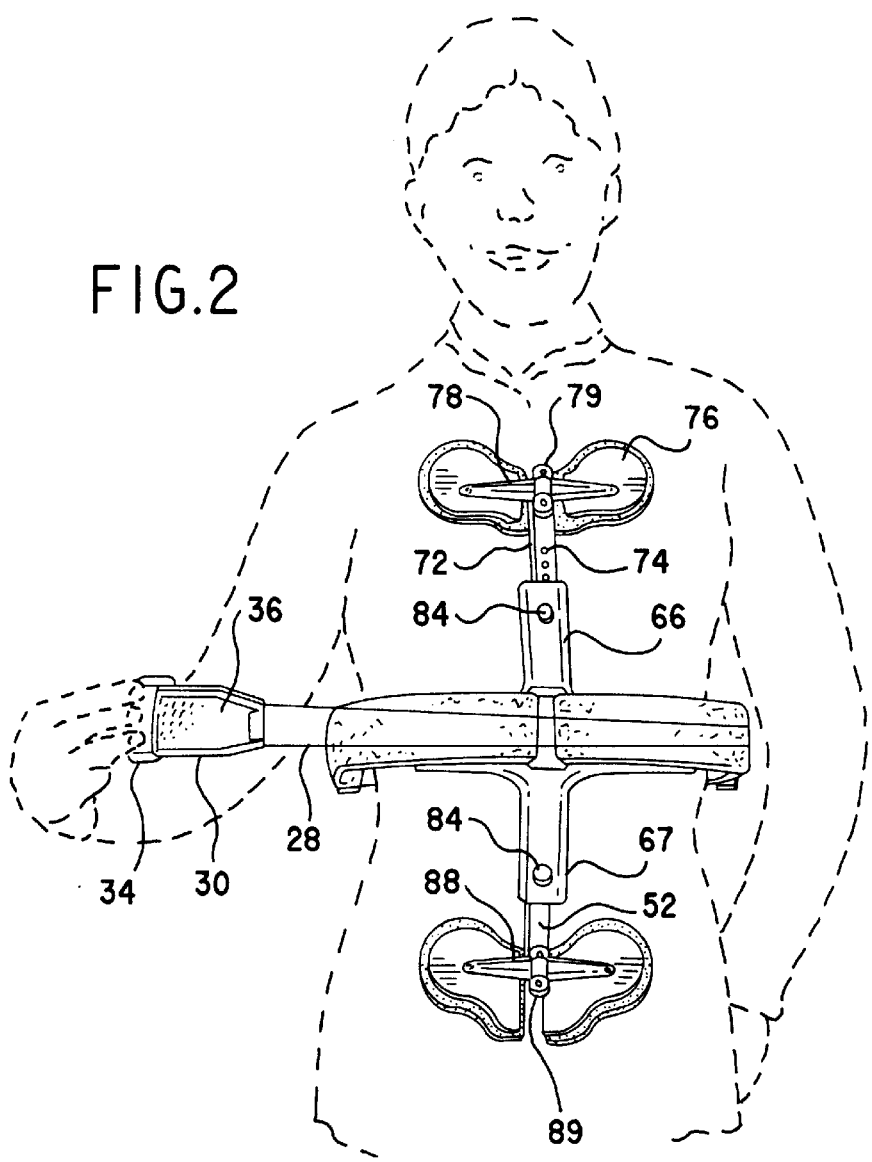
FIG. 2 illustrates a front view of a patient wearing the embodiment of the invention illustrated in FIG. 1.
Figure 3:
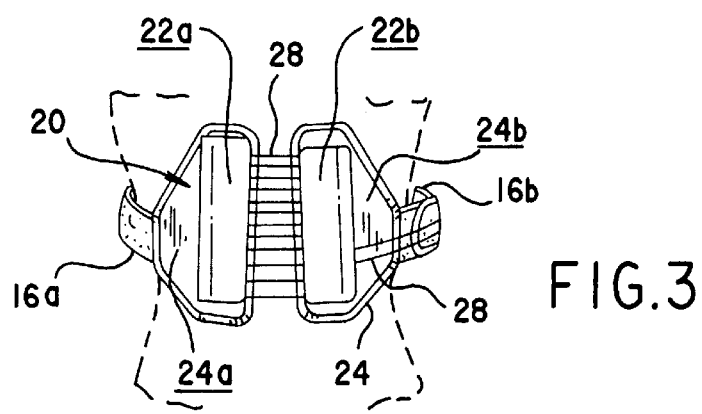
FIG. 3 illustrates a rear view of a portion of a patient wearing the embodiment of the invention illustrated in FIG. 1.

FIGS. 1 to 3 show a preferred embodiment according to the present invention. FIG. 1 illustrates the exterior side of a body cruciform anterior spinal hyperextension orthosis 10 in an extended position. The orthosis 10 includes a front or anterior portion 11 and a rear or posterior portion 12. The front portion 11 includes a rigid anterior cruciform brace assembly 60 which includes a cruciform-shaped centerpiece 62 having a center 63 and four arms 64, 65, 66, and 67 radiating outwardly from the center and disposed at right angles to one another. Preferably the center piece 62 is formed as a substantially rigid unitary cruciform base to which both the rear portion 12 of the cruciform anterior spinal hyperextension orthosis and the component parts of the rigid anterior cruciform brace assembly 60 are secured.

As best illustrated in FIGS. 2 and 3, the brace assembly 60 is positioned on the anterior portion of the patient's body while straps 16a and 16b secure the back portion 12 to the anterior portion 11, including the cruciform brace assembly 60, and wrap around the patient's body to position the rear portion 12 in contact with the lumbar region of the patient's posterior. Each of the arms 64, 65, 66 and 67 are open at their distal ends and are bowed inwardly toward the anterior portion of the wearer such that the tips of their free arms are disposed in a first plane which is spaced from and approximately parallel to a second plane lying substantially tangent to the outer surface of the center 63 of the cruciform base 62. The first plane is disposed closer to the wearer than the second plane. The cruciform base 62 is formed as a hollow unit having a cruciform-shaped chamber therein commensurate in shape to the cruciform base. Although the cruciform base 62 may be formed from a single piece, with certain manufacturing considerations in mind, it is preferred to form the hollow rigid cruciform base 62 from a cruciform shaped face plate or front piece 68 and a commensurately shaped cruciform-shaped rear plate (not shown) secured to the face plate by welding or by any suitable fastening (e.g., screws, bolts or rivets) or adhesive means. High tensile strength plastic or metal may be used to form the cruciform base and the other components of the cruciform brace assembly with metal being generally preferred.

Disposed at the upper and lower free ends of the hollow cruciform base 62 are sternal pad assembly 70 and pubic pad assembly 80, respectively, each of which is adapted to contact the anterior portion of the body in the sternum and pubic regions of the body, respectively, when the orthosis is placed on the wearer. Sternal pad assembly 70 includes an adjustment arm 72 formed as a metal or rigid plastic post, slidably receivable in the open upper portion of hollow arm 66 of the rigid hollow cruciform base 62. Along the length of the adjustment post 72 are a series of spaced apart apertures 74 intended to engage a locating mechanism in the arm 66 of the rigid hollow cruciform base 62. A preferred locating mechanism is a spring-loaded pin 84, the tip of which, when in a rest position, extends substantially through the outer face plate 68 into the hollow cruciform chamber formed within the cruciform base 62. When the outer mushroom-shaped head of the pin 84 is pulled outwardly against the biasing of a spring operatively associated with the pin and the rigid hollow cruciform base 62, the tip of the pin is substantially retracted from the hollow cruciform chamber. This permits the pin to engage and disengage any of the apertures 74 in the adjustment arm 72.

The sternal pad assembly 70 also includes a pad portion 76 pivotally secured to the upper end of the adjustment arm 72. The pad portion 76 is secured to, or formed as, a part of a horizontally arranged post 78 which is secured to left and right segments of the pad portion 76 and is rotatably secured substantially at its mid-point with a clamp or clasp 79 so as to form a hinge arrangement which permits the pad portion 76 to rotate in a plane substantially perpendicular to the body of wearer. This facilitates conformity with the individual sternal contours of the wearer of the device.

Arranged at the lower end of the rigid hollow cruciform base 62 is a pubic pad assembly 80, similar in components, function and shape to the sternal pad assembly 70, although the shape of the pad portion and pad may be varied somewhat to conform more closely to the contours of the pubic region. Adjustment arm 82, disposed vertically and slidably received within the open lower portion of hollow arm 67 of the rigid hollow cruciform base 62, also includes apertures (not shown), such as those found in adjustment arm 72, for adjusting the position of the pubic pad portion 86. The pubic pad portion 86 is appropriately shaped for the pubic region. Pubic pad assembly 80 also includes a hinge arrangement formed by a cross piece 88 affixed to symmetrical segments of the pubic pad portion 86 and rotatably secured by a clamp or a clasp 89 attached to adjustment arm 82 to rotate in a plane perpendicular to the body of the wearer. A locating means, preferably such as a biased pin arrangement 84, is also provided in arm 67. On the underside of each of the pad portions 76 and 86 are provided pads 77 and 87, respectively, adapted to be placed in contact with the wearer of the device. Preferably, these are high-density, compressible foam-type pads. The pads may be affixed directly to elements 76 or 86 by adhesive or may be removably secured thereto by means of complementary portions of hook-and-loop material to allow for cleaning and replacement.

Arranged horizontally at both free ends of the arms 64 and 65 of the rigid hollow cruciform base 62 are means for securing the rear portion 12 of the orthosis 10 to the front portion, which includes cruciform brace assembly 60. Although various means may be employed to secure the rear portion 12 to the front portion 11, preferred are fastening means which permit the wearer to both assemble and disassemble or partially assemble and disassemble the device for rapid donning and doffing, as well as means for facilitating rapid adjustment of the cruciform anterior spinal hyperextension device. Accordingly, at the open distal ends of each hollow side arm portions 64 and 65 of the rigid hollow cruciform base 62 is received an adjustable arm (92 and 94). The means for adjusting these laterally disposed arms 92 and 94 preferably includes, in part, the same type of adjustment means as used with the sternal pad assembly 70 and pubic pad assembly 80. This includes rigid metal or plastic arms 92 and 94 provided with spaced apart apertures (not shown) along the length of each adjustment post 92 and 94. As previously described with regard to arms 66 and 67, spring-loaded pins 84 are movably secured to each of the arm portions 64 and 65 to retractably engage the apertures, thereby permitting adjustment of each arm by slidably moving the arm which telescopes within the hollow portion of the cruciform base 62 until the desired location is reached and engaging the pin 84 in the nearest appropriate aperture of the arm 92 or 94, whereupon the retracted pin 84 is released to engage that aperture. At the outer ends of each adjustment piece 92 and 94 are provided securing or fastening pieces 96 and 95, respectively, formed from metal or rigid plastic and secured to the adjustment arms. Preferred fasteners 95 and 96 each include slots of suitable width to accommodate straps 16a and 16b provided on the rear portion 12 of the cruciform anterior spinal hyperextension orthosis of the invention.

The rear portion 12 of the cruciform anterior spinal hyperextension orthosis of the invention includes a paraspinal support 24 formed in two segments 24a and 24b, which contact the posterior portion of the body of the wearer. The two segments of the paraspinal support 24 include complementary portions of means used to secure the rear portion 12 to the front portion 11 forming the rigid anterior cruciform brace assembly 60. Preferably, these include straps, webs or belts 16a and 16b which, in the preferred embodiment are disposed at the lateral edge of each segment 24a and 24b, engage the fasteners 95 and 96 formed at the free ends of lateral, horizontally disposed adjustment arms 94 and 92, respectively. Preferably, the straps 16a and 16b pass through slots 97 and 98, respectively, provided in the buckle-type fasteners 95 and 96 and are secured by any suitable means, such as snaps, buckles, etc. Preferred, however, are complementary portions of hook-and-loop material 18a and 18b formed on front and rear surfaces and appropriate positions along the belts 16a and 16b to allow the belts to pass through the slots formed in elements 95 and 96 and folded back on themselves to suitably engage complementary portions of the hook-and-loop material and thereby secure the straps in place. Use of hook-and-loop material also allows for incremental adjustment of the belts which is not typically encountered by most other means of adjustment.

The paraspinal support 24 serves several functions in the cruciform anterior spinal hyperextension orthotic device of the invention. First, it serves as one of the points for the three-point fixation system of the present invention. The paraspinal support assembly 24, positioned at the lumbar region of the back, serves to position and anchor the orthoses to the posterior of the wearer. The posterior anchoring, in combination with the anterior anchoring of the orthotic device at both the sternum and pubic areas are generally the only points of contact of the cruciform anterior spinal hyperextension orthosis with the body of the patient. This may be contrasted with other conventional cruciform anterior spinal hyperextension systems in which not only is there contact between the orthoses and the three aforementioned body areas, but conventional devices typically contact the body of the patient at the sides of the torso. Accordingly, with a greater number of contact points there results increased discomfort and an increased likelihood of chafing where the device contacts the body, resulting from misadjustment of the device. The present invention minimizes the number of points of contact and facilitates quick and easy adjustment and readjustment.

The inner portion of the paraspinal support 24, preferably includes a cushioning material. Preferred is a perforated "waffle" type material (not shown), which may be either adhered directly to the inner surface of the segments of the paraspinal support with adhesive or may be secured thereto with complementary portions of hook-and-loop material. This facilitates removal for cleaning.

While an initial gross adjustment of both the position and tension may be made to the device using the fastening and adjustment straps 16a and 16b, and perhaps with the arms 72, 82, 92 and 94, fine adjustments of the device and subsequent readjustment of the device with regard to proper tensioning, such as when the patient changes physical position, may be achieved with the adjustment means incorporated into the paraspinal support 24. Thus, placed at adjacent edge portions 14c and 14d, respectively, of juxtaposed support segments 24a and 24b, which may be formed as physically separate pieces or portions of the same paraspinal support member, is located at least one and, preferably only one, pulley set 20 which includes separate pulley banks 22a and 22b. The type of pulley sets which are preferred in the present invention are described in greater detail in copending U.S. patent application Ser. No. 09/334,649 and U.S. patent application Ser. No. 09/420,408, specifically incorporated herein by reference. Within each bank of pulleys 22a and 22b are arranged a sufficient number of pulleys 26 (FIG. 4) to provide a mechanical advantage to the device of at least 6:1. A cable 28 is wound around each pulley in each bank of a set of pulleys in series and in alteration such that when the two free ends of cable 28 are pulled, tension is increased on the cable and the two juxtaposed segments 24a and 24b are pulled closer to one another, thereby finally adjusting the orthotic device.

The free ends of cable 28 are secured to a handle device 30, which is provided with a grasping portion 34, preferably in the shape of a bail. Rather than leaving the handle 30 to dangle freely from one of the banks of the pulley set, a releasable fastener is provided to removably secure the handle to a portion of the device. Preferably, the handle has a portion of a hook-and-loop material 36 affixed to a portion of the handle to removably engage a complementary hook-and-loop material 18a on the belts 16a or 16b.

When it is desired to adjust or readjust the fit of the device, by tensioning the pulley system, the patient merely needs to grasp the handle 30 and increase the tension or slack of the cable 28. Because of both the convenience of the handle and the mechanical advantage, small changes in adjustment of the orthotic device may be accomplished within several seconds.

In all, the cruciform anterior spinal hyperextension orthosis of the invention allows for numerous modes of adjustment to provide a custom fit of the device and facilitate rapid readjustment. The various modes of adjustment of the device include:

a) vertical positioning of the sternal assembly 70 by releasing pin 84 and movement of adjustment piece 72;
b) vertical adjustment of pubic pad assembly 80 by retracting pin 84 and movement of adjustment piece 82;
c) horizontal adjustment by retracting pin 84 and moving adjustment piece 92 and fastener 96;
d) horizontal adjustment by retracting pin 84 and moving adjustment piece 94 and fastener 95;
e) repositioning of removal and adjustment strap 16a;
f) readjustment of removal and adjustment strap 16b;
g) retensioning of pulley set 20 using adjustment handle 30 and cable 28.

It is readily apparent that the above-described has the advantage of wide commercial utility. It should be understood that the specific form of the invention hereinabove described is intended to be representative only, as certain modifications within the scope of these teachings will be apparent to those skilled in the art.

Accordingly, reference should be made to the following claims in determining the full scope of the invention.

What is claimed is:

1. A cruciform anterior spinal hyperextension orthosis comprising:
   (a) a front portion having a rigid anterior cruciform brace assembly provided with (i) movable upper and lower arms extending therefrom and arranged vertically, (ii) two laterally disposed movable arms extending therefrom horizontally, and (iii) body contact pads rotatably secured to the free ends of each of the upper and lower vertically disposed arms;
   (b) a rear portion adjustably secured to said front portion and having (i) a paraspinal support formed in two juxtaposed segments, (ii) a pulley system comprising at least one set of pulleys having two pulley banks each having a plurality of pulleys, each bank disposed proximate to an adjacent edge of the juxtaposed segment, and (iii) a cable running through each pulley of each bank of pulleys in the at least one set in alteration and in series and linking together each of the two juxtaposed segments; and
   (c) adjustable means of securing the front portion to the rear portion including: (i) two straps, respectively removably attached to lateral edges of the two juxtaposed segments and adapted to be secured to (ii) two strap engaging devices, respectively, attached to each of the laterally disposed movable arms.

2. The cruciform anterior spinal hyperextension orthosis of claim 1, wherein the rigid anterior cruciform brace assembly further includes a hollow cruciform-shaped centerpiece having a center and four arms radiating outwardly from the center at substantially right angles to one another, each of the four arms of the hollow cruciform-shaped centerpiece receiving one of the movable upper and lower arms and the laterally disposed movable arms.

3. The cruciform anterior spinal hyperextension orthosis of claim 2, wherein each of the movable upper and lower arms and the laterally disposed arms are bowed inwardly toward the rear portion such that their distal ends are disposed in a first plane which is spaced from and approximately parallel to a second plane lying substantially tangent to an outer surface of said center of said centerpiece.

4. The cruciform anterior spinal hyperextension orthosis of claim 1, wherein each of the movable upper and lower arms and the laterally disposed arms are incrementally adjustable.

5. The cruciform anterior spinal hyperextension orthosis of claim 1, wherein said two straps include complementary portions of hook-and-loop material, such that after the straps are secured to the two strap engaging devices, they may be folded back on themselves in order for the complementary portions of the hook-and-loop material to engage each other.

6. The cruciform anterior spinal hyperextension orthosis of claim 1, wherein the cable is secured to a handle.

7. The cruciform anterior spinal hyperextension orthosis of claim 6, wherein the handle is provided with a portion of a hook-and-loop material.

8. The cruciform anterior spinal hyperextension orthosis of claim 1, wherein each of the body contact pads is mounted on a pad mounting portion which is fixed by a hinge arrangement to the distal ends of each of the upper and lower vertically disposed arms, the hinge arrangement permitting each pad mounting portion to rotate in a plane substantially perpendicular to the body of a wearer.

9. The cruciform anterior spinal hyperextension orthosis of claim 8, wherein each of the body contact pads is removably mounted on the pad mounting portion using complementary portions of hook-and-loop material affixed to commensurate surfaces of each pad and pad mounting portion.

10. The cruciform anterior spinal hyperextension orthosis of claim 1, wherein said at least one set of pulleys comprises one set of pulleys.

* * * * *